United States Patent
Maccioni Baraona et al.

(10) Patent No.: US 8,784,804 B2
(45) Date of Patent: Jul. 22, 2014

(54) NUTRACEUTICAL COMPOSITION THAT COMPRISES EXTRACT OF ANDEAN SHILAJIT, FOR PREVENTING AND/OR TREATING NEURODEGENERATIVE DISEASES AND/OR THE COGNITIVE DETERIORATION ASSOCIATED WITH CEREBRAL AGING

(75) Inventors: Ricardo Maccioni Baraona, Santiago (CL); Luis Quiñones Sepúlveda, Santiago (CL); Iván Saavedra Saavedra, Santiago (CL); Ricardo Sandoval Salas, Santiago (CL); Victor Sandoval Salas, Santiago (CL)

(73) Assignee: Centro Internacional de Biomedicina (ICC), Santiago (CL)

( * ) Notice: Subject to any disclaimer, the term of this patent is extended or adjusted under 35 U.S.C. 154(b) by 0 days.

(21) Appl. No.: 13/496,140

(22) PCT Filed: Oct. 8, 2010

(86) PCT No.: PCT/CL2010/000043
§ 371 (c)(1),
(2), (4) Date: Mar. 14, 2012

(87) PCT Pub. No.: WO2011/041920
PCT Pub. Date: Apr. 14, 2011

(65) Prior Publication Data
US 2012/0269794 A1    Oct. 25, 2012

(30) Foreign Application Priority Data
Oct. 9, 2009 (CL) .................................. 1956-2009

(51) Int. Cl.
*A61K 38/46* (2006.01)

(52) U.S. Cl.
USPC .......................................................... 424/94.1

(58) Field of Classification Search
None
See application file for complete search history.

(56) References Cited

U.S. PATENT DOCUMENTS 5,405,613 A * 4/1995 Rowland ....................... 424/439

OTHER PUBLICATIONS

Talbert, R. Aug. 30, 2004 [Retrieved from the Internet on: Oct. 30, 2013]. Retrieved from: <URL: http://www.therdsf.org/wp-content/uploads/2012/12/shilijitNEW-1.pdf>.*

* cited by examiner

*Primary Examiner* — Amy L Clark
(74) *Attorney, Agent, or Firm* — Gottlieb, Rackman & Reisman, PC

(57) ABSTRACT

The present invention relates to a potent antioxidant neuroprotective nutraceutical composition that comprises blending extract of Shilajit (250 to 500 mg) and folic acid (200 to 400 μg), together with small amounts of vitamins B6 (20 to 40 μg) and B12 (4 to 8 μg) consumed per day. This composition can be used to prevent and to treat neurodegenerative diseases or episodes of cognitive deterioration arising from various pathological conditions. The use thereof is indicated in the treatment of Alzheimer's disease and senile dementia as the pathological conditions preferably to be treated. The composition is suitable for direct human consumption by mouth, either in solid form as a powder or as a suspension of the extract, as a food additive or as a nutraceutical agent. It may be formulated as a nutraceutical agent to be included as an ingredient in beverages or as a drug in conjunction with permitted excipients.

17 Claims, No Drawings

NUTRACEUTICAL COMPOSITION THAT COMPRISES EXTRACT OF ANDEAN SHILAJIT, FOR PREVENTING AND/OR TREATING NEURODEGENERATIVE DISEASES AND/OR THE COGNITIVE DETERIORATION ASSOCIATED WITH CEREBRAL AGING

INVENTION BACKGROUND

It has been estimated that the USA invests more than $178 billion dollars annually in direct and indirect costs to control Alzheimer Disease (AD). With a percentage of the population over 65 years old (in Chile it is over 12%), the number of people with AD will increase rapidly and proportionally. If early diagnosis technologies for AD are not found soon, as well as interventions for its treatment, the number of people who will develop the disease will surpass health systems. Since our group has conducted research for more than 30 years in this field and we have made some of the most relevant discoveries in the world, we are in the best position to innovate and find effective solutions for its prevention, early detection and treatment. Thus our findings contribute to AD prevention, to its diagnosis (molecular markers and neuroimage technologies), and now to its treatment. We are developing new drugs for controlling the disease, in addition to cognitive stimulation technologies through software designed to improve patients' quality of life and to correct memory disorders. We now offer a pharmaceutical formulation that, according to our previous research, helps to prevent and control brain disorders leading to AD and other neurodegenerative diseases, among them oxidative stress, neuroinflammation and the gradual loss of neurons.

At present the FDA has approved only 5 drugs for AD treatment, and the use of some of them has been extended to other dementias (vascular dementia, Lewy bodies dementia, frontotemporal dementia due to taupathies, etc.) (Maccioni & Perry, 2009).

Four of them inhibit AChE enzyme (acetil colinesterasa) and their pharmacologic activity is aimed at compensating the cholinergic loss taking place in AD. None of them succeeds in healing this pathology and their action is rather palliative, diminishing the progress of symptoms, as they do not control AD's etiopathogenesis. These drugs are: Tacrine® (almost not used any more due to its hepatotoxic condition), Donepecil, Rivastigmine and Galantamine. The last three cover more than 80% of the markets and in spite of their very low effectiveness their sales amount to billions of dollars around the world.

Each one of them is sold in pharmaceutic forms under commercial names given by different laboratories which produce and put them on the market. They are highly expensive but have not managed to stop the disease's progression. The other drug is Memantine, which acts at another level, on NMDA receptors blocking exitotoxicity processes and the entrance of calcium into brain cells. Its market is still reduced as it has been commercialized for a shorter period of time. Its use is reserved essentially for advanced stages of the disease, but it is also palliative as it does not heal AD due to its incapacity to control endogenous mechanisms leading to the pathogenesis of this disease. On the other hand, other molecules are undergoing research and clinical testing, for example: (i) growth factors such as Cerebrolysin® which could be promising if the action—not yet demonstrated—of neurotrophic factors can be proven, and (ii) inhibitors of gamma secretase and vaccines guided towards senile plaques, definitively not effective due to the fact that senile plaques, neuropathological alterations formed by beta amiloid, are not responsible for AD and recent studies strongly disprove the amiloid hypothesis. These drugs, in which several pharmaceutic industries have invested billions of dollars, have not been successful because they do not respond to modern hypothesis of the pathology, as the tau and neuroimmunomodulation hypotheses (Maccioni & Perry, 2009).

AD's pathogenesis is directly related to the self aggregation of tau as the common final path for altered mechanisms of signal transduction between glial and neuronal cells, as a result of a series of danger signals in which innate immunity phenomena are involved (Maccioni et al., 2009). Therefore two types of the latest generation drugs would be the most promising for an effective AD treatment and could in the future replace the five first-generation molecules that have not proven to be effective. These new molecules are:

a) Inhibitors of the tau pathologic autoagregation in PHF-type filaments and finally in neurofibrillary tangles (NFTs), among which the drugs of our patent are present, the "quinolines", and exert an effective action at this level.

b) Modern antiinflammatories that control over activation of TNF α proinflammatory cytokine, including etanercept.

The significant progress in the knowledge of the molecular aspects promoting neurodegeneration in relation to cognitive deterioration, including the changes in the functioning of the tau protein, inflammatory processes and oxidative stress, among others (Maccioni et al., 2001, 2006, 2009, Quintanilla et al., 2004; Orellana et al., 2005; Fernández et al., 2008; Farias 2010), is contributing nowadays to a more open-minded attitude in the search of new tools to treat these disorders. In Chile the prevalence of cognitive deterioration in the population, based for this diagnosis on a MiniMental<13 score is 7.9% in the age between 60-69 years, 18% between 70-79 years and 48% at 80 or more. It is estimated that the population with this kind of deterioration is over 280,000 people (Ministry of Health). This same study revealed a significant greater prevalence according to the literacy level: for people with only primary studies, the prevalence was 20.3%, for those with high school studies, 3.7% and for those with university studies, 2.6% (Ministry of Health, First Health Survey, 2003).

Neurodegenerative disorders are linked to an extensive and gradual neuronal loss, and associated to the ethiopathogenesis of this illness are the tau neurotoxic aggregates as well as the neurofibrillary tangles (NFTs). These are formed by a protein associated to the neuronal cytoskeleton named tau, which is hyperphosphorylated in the brains of AD patients (Kurt et al., 1997; Maccioni et al., 2001; Maccioni et al., 2004). Via unknown mechanisms, tau undergoes important modifications such as abnormal phosphorylation due to the deregulated activity of various kinases and phosphatases affecting their normal biological function (Zambrano et al., 2004). Under these circumstances tau begins to aggregate itself and produces NTFs, which are structures constituting a hystopathological marker, characteristic of AD (Maccioni et al., 2003).

The product of our neuroprotective formulation blocks the neuroinflammatory processes where the hyperphosphorylation of the tau protein takes place (Maccioni et al., 2009). On the basis of our hypothesis of the presence of tau in the ethiopathogenesis of AD, we have been researching on the disaggregating action of different molecules on NFTs, the main hystopathological injury found in brains of individuals presenting this pathology. After several attempts with drugs that disassemble amyloid's senile plaques, most of the efforts made worldwide to control cognitive disorders are being directed at present towards molecules with antiinflammatory activity and neuroprotectors.

In this context, and due to the dramatic increase in life expectancy at the global level, to find viable solutions for the treatment of cognitive disorders constitutes one of the greatest challenges faced by the pharmaceutical and biotechnological industry. There exist very few effective pharmaceutical formulations that act as neuroprotectors or cognitive function restorers; among them the most recent is Memory XLR, which contains essentially vitamins and S-adenosyl-metionin and has shown relatively promising results at the clinical level (Chan and Shea, 2007). This confirms the enormous importance of generating natural products with nutraceutical activity that stimulate brain function, with no adverse effects for human beings, and with a tested efficiency and safety. This is the foundation of our effort to generate a formulation containing a nutraceutic with a highly antioxidant potential. Our nutraceutical formulae contains more than 96 times the antioxidant power present in cranberry concentrates and Noni, among others, measured by the TAR index, the Total Antioxidant Reactivity and evaluated in TROLOX equivalents. Thus our nutraceutic combines its high potency antioxidant effects with vitamins $B_6$ and $B_{12}$ plus folic acid, all of them key neuroprotective elements for brain activity and also for avoiding cognitive deterioration. The nutraceutic belonging to this formulation is a 100% native product, the "Andean Shilajit", obtained from millenarian organic concentrates derived from bryophyt plants from the north of Chile, found in the subsoil of arid zones, with a high acid fulvic content, a product with a proven antioxidant power in addition to an anti-inflammatory activity. Besides these characteristics favoring brain health, folic acid jointly with vitamin $B_{12}$ are key components to halt metabolic processes generating homocysteine, a neurotoxic activity. High homocysteine anaemia in patients is an important risk factor for cognitive deterioration. Moreover, vitamin $B_{12}$ has a synthesis which decreases in the brain as people begin to age so it is advisable to supplement it.

DETAILED DESCRIPTION OF THE INVENTION

The invention to be protected consists of a synergic composition to be used in the prevention and treatment of neurodegenerative diseases such as Alzheimer and other dementias associated to aging. The composition contains Shilajit extract, folic acid, vitamin $B_6$ and $B_{12}$. Shilajit is a millenary sacred plant with a large quantity of healing properties, it is very effective in reducing fatigue and works as a natural energizer. This herb growing in the Himalayas mountains contains fulvic acid and humic acid, natural antioxidant substances that help to delay cell aging, they attack tumor generation, help to neutralize toxins and to improve the availability of minerals in the body making them bioactive and bioavailable for our body. We have recently found this plant in the Andean sector of the north of Chile (Andean Shilajit). Shilajit contains roughly 85 types of minerals in their ionic form which are vital to maintain energetic metabolism balanced in the body. Shilajit's minerals are not similar to the ones normally sold in the market as food supplements because these have ionic form and have been previously absorbed by plants and have returned to the soil, so they are easily absorbed by human cells. A few patents exist associated to the Shilajit nutraceutic around the world vindicating the advantages and qualities of the individual product. U.S. Pat. No. 5,405,613 refers to the use of Shilajit or its extracts in vitamin or mineral compositions and methods to restore the energetic balance or to increase the bioenergetic field in mammals. Inventors found that Shilajit,"has a vibrational field substantially stronger than that of any other vitamin, mineral, alimentary substance or herb". They also discovered that when adding small quantities of Shilajit to a vitamin or mineral formulation the energetic properties increased. U.S. Pat. No. 6,440,436 describes a Shilajit composition having an abundance of bioactive components useful for countering toxic agents, as well as for personal, pharmaceutical and nutritional care.

Below is a description of the main characteristics and attributes of the components of this invention using Andean Shilajit in addition to other food supplements: Fulvic Acid. It is a Shilajit component, a completely natural and organic extract rising from the deposit of a plant 75 million years ago and corresponding to the higher cretaceous period. It contains a large quantity of photochemicals, biochemicals, antioxidants, free radicals suppressors, nutrient substances, enzymes, hormones, aminoacids, antibiotics, antivirals, antimycotic substances, among other elements. Fulvic acid contains about 74 essential organic and mineral compounds dissolved with 42% of solid acid food. It improves mineral availability in the body, regenerates and extends residence time of essential nutrients in the cells, diminishes the damage produced by toxic compounds, heavy metals, free radicals and its consumption improves permeability for the digestive and circulatory systems and cell membranes. In the $15^{th}$ century, during the Ming Dinasty, Li Shi Zhen registered, in the pharmacologic abridgement of Medical Matters, the incidents of the use of "Wujinsan" (golden medicine) which contained fulvic acid as an active ingredient in the treatment of infectious ulcerous diseases, thus involving fulvic acid as an agent for anti-inflammatory coagulation and for efficient blood.

Before 1978, fulvic acid had been used in hospitals and on population in general to treat successfully a wide range of diseases; nonetheless, there was very scarce research on its therapeutic mechanism. Due to lack of clinical data and absence of clinical trials, there were still doubts as to the therapeutic use of fulvic acid. From that time onwards, a group of medical schools and hospitals in China have begun to carry out comprehensive studies on the toxicology and pathology of fulvic acid and its clinical uses. Hundreds of studies have been published in China, some of them appearing in international newspapers, in addition to some reports presented in various meetings outside China. The pharmaceutic companies in the hands of Dr. Shanxi in Gongxian, Henan and in Kunming, Yunnan produced the fulvic acid that was then approved by the Chinese drug administration due to its non-toxicity, for oral as well as external uses. The pharmaceutic use of fulvic acid has been approved by the provincial drug administration on the basis of its efficacy and safety, both internally and externally. At present, it is recognized that fulvic acid acts as an important protective agent and a powerful natural electrolyte that can restore the electric balance of damaged cells, neutralize toxins and eliminate food intoxication in a matter of minutes. It is created in the soil by microorganisms with the aim of transporting minerals and nutrients from there to the plants. Then, complex photosynthesis reactions produce the components from different zones of the plant. Sugars coming from complex carbohydrates flow along the whole plant for nutrition. Some return to the roots where microorganisms are fed, producing fulvic acids as a complex with minerals and nutrients, and the cycle begins again. In plants, fulvic acid stimulates metabolism, provides breathing, increases proteins and the activity of multiple enzymes, improves permeability of cell membranes, their division and elongation, it facilitates chlorophyl synthesis, drought tolerance, protects soil pH and from microbe attacks, contributes to electrochemical balance as a donor or acceptor, disintegrates silicone in order to release essential nutrient substances, detoxificates contaminants such as pesticides and herbicides.

When minerals contact with fulvic acid, in an aqueous environment, they dissolve naturally in an ionic manner and, literally, they become a part of it. Once minerals are in the fulvic acid complex, they become bioactive, bioavailable and organic. For that reason, when elemental minerals are transformed into an organic state through a natural chemical process implying fulvic acid and photosynthesis, they are safe to be used both in human beings and animals. Fulvic acid is found and extracted, preferentially, in the Himalayas, but it was recently discovered in the northern region of Chile (Andean Shilajit). The latter is richer in fulvic acid than the Shilajit from the Himalayas. It has been scientifically demonstrated that among its multiple benefits it helps human tissue to grow and regenerate, it lowers strain, stress, general weakness and fatigue, acting as an antioxidant. Its use as medication helps to slow down cell aging.

Another important aspect of the use of fulvic acid consists in a general health improvement through the fight against several diseases associated to mineral deficiency in the body. Organic fulvic acids are created precisely by microorganisms in the soil with the goal of transporting minerals and nutrients from the soil up to the plant, which would help to perform the same function in the human body. In ancestral medicine it was considered a panacea and used to increase sexual and spiritual energy, the same vigor that tension and anxiety wither. In India the indigenous medicine system uses it to combat various illnesses such as: kidney and bladder affections, anaemia, asthma, chronic bronchitis, nervous weakness, diabetes, fermentative dyspepsia, hepatosplenomegaly, hysteria, sexual neurasthenia, digestive disorders, etc.

Pharmacologic Studies Achieved with Fulvic Acid:

1. As an antiinflammatory agent: The efficacy of hydrogenated cortisone with respect to fulvic acid changes according to the site of its origin and the extraction method used. (i) Fulvic acid inhibits an enzyme discharged in the infected area and moreover regulates the zinc and copper levels of the trace elements, thus activating the dismutase that contain zinc and copper.
2. Stimulates blood circulation and enhances coagulation: Many diseases are caused by the malfunctioning of circulation in the blood's capillary system. The therapeutical effect of fulvic acid is a result of its capacity to restore and improve circulation in the blood's capillary system. On the other hand, fulvic acid also serves as a blood coagulant when there is tapping or blood filtrating from the vascular layer.
3. Digestive ulcers: The healing effects of fulvic acid are the result of its capacity to stimulate blood circulation in the stomach wall and its ability to inhibit the secretion of acid-producing cells. It also stimulates the secretion of glands that have the capacity to protect the stomach's inner wall, thus preventing ulcers.
4. Immune System: There is reason to believe that if fulvic acid is injected in the abdominal area, the size of the thymus increases in animals under testing, together with the augmentation of macrophage activity. A dosification of 5 mg/kg of weight injected in the abdominal area is beneficial. Nonetheless, doses over 50 mg/kg showed the opposite effect, that is, the size of the thymus is reduced.
5. Endocrine System: Fulvic acid regulates the abnormal secretion of the thyroid hormone as a result of its power to regulate cyclic at the cell level.
6. Cancer: Fulvic acid, in general, does not kill tumor cells; nonetheless, it serves as a regulator agent in the immune system and can be used jointly with other antineoplastic medicines.

Clinical Uses of Fulvic Acid

1. Antiinflammatory and blood coagulant: In many clinical cases infections were accompanied by blood filtering into the area or bleeding ulcers. Fulvic acid moderates ulcerous conditions on the basis of its antiinflammatory nature, acting at the coagulation level and the whole body.
2. Infection of the cornea: Fifty-three cases were studied and treated with fulvic acid eye drops and intramuscular injections, obtaining a rate of success of 94.2%. The study was carried out in an eye clinic at the Shaoxin hospital, Zhejiang province, China.
3. Acute gastrointestinal hemorraghe: 160 cases were studied and treated with fulvic acid in oral and injectable form, with a rate of success of 95.6%. The studies were carried out at Internal Medicine at the Tongren Hospital, Beijing, China.
4. Skin ulcers: Fifty-one cases were studied and treated with a fulvic acid bath and minerals with a rate of success of 92.2%. The studies were carried out at Internal Medicine at the Tongren Hospital, Beijing, China.
5. Rheumatoid arthritis: A large number of cases were studied and treated with the fulvic acid bath mixed with minerals and in oral form (capsules), with a rate of success of 92%. de éxito. The studies were carried out at the Haidian Hospital, Beijing, China.
6. Hemorrhoids: Several thousands of cases were studied and treated with the fulvic acid preparation. The rate of success was so high that the Chinese medical authorities developed an over-the-counter (OTC) medicine for its national distribution. The studies were carried out at the hospitals of Erlonglu in Beijing and Kunming in Yunnan, China.
7. Esophageal Cancer: disease's incubation period: 27 cases were studied and treated using a solution of fulvic acid in water during two years. The hit rate was 100% in the progression of the prevention of the tumor in its cancerous state. The studies were carried out by Hongji Xie, et al.
8. Overactive thyroid: 33 cases studied and treated during 6 months with fulvic acid in oral form (capsules) with a rate of success of 0.9%. The studies were carried out at the Tongren Hospital, Beijing, China.

In short, as a result of common efforts contributed by researchers and their basic clinical studies on science, the fulvic acid component, originating from humic acid, has proven to be an effective and safe remedy for a wide variety of illnesses. This contribution has raised the curiosity and interest of foreign scientists, as stated in "The recent progress in Chinese medicine" published in Singapore and in "Fulvic Acid" published in Germany.

Folic Acid (Vitamin B9)

Discovered in the 1940's, folic acid (B9) is considered a water-soluble vitamin pertaining to the B complex. It is also known as folacin or folate whose etymology comes from the latin "folium" meaning leaf. The vitamin is essential to achieve all of our body's functions. Its great importance lies in the fact that folic acid is fundamental at the cell level to synthetize DNA (deoxyribonucleic acid), responsible for the transmittal of the 11 genetic characters and also to synthetize RNA (ribonucleic acid), required to form the body's proteins and tissues and other cell processes. Therefore, the presence of folic acid in our body is indispensable for the correct cell division and duplication. Folates work together with vitamin $B_{12}$ and vitamin C in the use of proteins. It is important to point out that folic acid is basic in the formation of the hemo group (part of hemoglobin containing iron), that is why it is related to the formation of red blood cells. Folic acid also benefits the cardiovascular system, the nervous system and the neurological fetal formation, among others. Given its great importance for human beings, much of the foodstuff we consume nowadays is enriched with folic acid. This acid is formed in the intestine from our colonic flora. It is absorbed mainly in the small intestine (jejunum), then it is distributed in the tissues via blood circulation and is stored in the liver and is excreted through urine and feces. A large number of research studies have permitted to observe that folic acid is necessary in the formation of red blood cells, it reduces the risk of the appearance of defects in the neural tube of the fetus, such as spina bifida and anencephaly, diminishes the occurrence of cardiovascular diseases, prevents some types of cancer, helps to increase appetite and stimulates the formation of digestive acids.

Vitamin $B_6$ (Pyridoxine)

Vitamin $B_6$ is a water-soluble vitamin, this implies that it is eliminated through the urine and therefore must be replaced daily with the diet. Vitamin $B_6$ is in fact a group of three chemical compounds called pyridoxine (or pyridoxol), pyridoxal and pyridoxamine. The phosphorylated derivatives of pyridoxal and pyridoxine, that is, pyridoxal phosphate (PLP) and pyridoxamine phosphate (PMP) perform coenzyme functions. They participate in many enzymatic reactions of the metabolism of aminoacids and their main function is the transfer of amino groups; therefore, they are transaminase coenzymes, enzymes that catalyze the transfer of amino groups among aminoacids. Those coenzymes act as temporary carriers of amino groups.

This vitamin is often known popularly as the "women's vitamin" since it has been sustained that it contributed to relieve premenstrual syndrome (irritability, downheartedness, etc.). Scientific studies carried out on this matter have not achieved clear and conclusive results.

Vitamin $B_6$ intervenes in the elaboration of brain substances regulating the mood such as serotonine, being able in some cases to help some people suffering from depression, stress and sleep disorders. This vitamin is very popular among sportsmen and sportswomen because it increases muscular performance and energy production. The latter is due to the fact that when there is the need to make a greater effort it favors the release of glycogen stored in the liver and muscles. It can also contribute to lose weight because it helps our body to obtain energy from accumulated fat.

It is known that our body requires Vitamin $B_6$ to adequately synthesize antibodies and erythrocytes, it is very important for an adequate absorption of vitamin $B_{12}$ and magnesium. It also helps in cases of a tendency to have night-time muscular spasms, leg cramps and dead limbs, it favors iron absorption and intervenes in myeline formation. In addition it can help reduce mouth dryness caused by medication (specially by some antidepressants).

Gestational and nursing diabetes have been linked to a vitamin $B_6$ deficiency that would bring about a low level of insulin and thus would hinder the entrance of carbohydrates in cells. Diabetics often observe they need less insulin if they take vitamin $B_6$, so they must supervise their glucose levels and adapt the insulin dose.

Vitamin $B_6$ is found in wheat germ, meat and vegetables, food rich in refined sugars, additives and natural dyes.

Vitamin $B_{12}$ (Cobalamin)

This is a complex B water-soluble vitamin, important for metabolism, it helps to form blood red cells and to maintain the central nervous system. It is found in eggs, beef, chicken meat, seafood, and also in milk and its by-products.

Low levels of vitamin $B_{12}$ may cause anaemia, numbness or tingling sensation in arms and legs, weakness and loss of balance. Additionally, people who have undergone surgery in specific parts of the small intestine or stomach are also subject to present a deficiency if they do not take supplements of this vitamin.

Surprisingly and unexpectedly we have observed that the mixture of Shilajit and folic acid, together with small quantities of vitamins $B_6$ and $B_{12}$ generate beneficial effects as an antioxidant agent and cell protector, especially in nerve cells. These effects are much greater than the individual effects of the agents forming the mixture. This strongly suggests the use of this composition in neurodegenerative diseases such as Alzheimer. These synergetic effects are observed presumably due to Shilajit's neuroprotector characteristics, in addition to the homocysteinemic activity of the mixture between folic acid and vitamin $B_{12}$, which, together with vitamin $B_6$'s antidepressant and antistress effect generates a new nutraceutic product with great strength as a neuroprotector to prevent and treat neurodegenerative disorders.

The composition is appropriate for direct oral human consumption, either in solid form or in a solution to be added to food or as a nutraceutic agent; it can be an ingredient of energizing beverages or can be formulated as a medication together with authorized excipientes.

EXAMPLES

The following are our preferred—but not exclusive—examples of our invention:

Example 1

Formulation Example

As the composition's preferred formulation we have:
Folic Acid: 200 µg
Vitamin $B_{12}$: 4 µg
Vitamin $B_6$: 200 µg
Shilajit: 250 mg and Excipients: c.s.p. 350 mg Eamples 2

Example of the Formulation's Production

For the production of one 350 mg capsule of our medication we proceed in the following way:
  The components of the composition illustrated above are mixed in the previously described proportions and in a random mode.
  Then the composition is mixed with corn maltodextrin in enough quantity for a 350 mg powder capsule.

Example 3

Administration and Dosage for Neurodegenerative Diseases

The capsule may be administered in the following diseases and in the indicated dosage:
a. Alzheimer disease: 1 every 12 hours
b. Senile dementia, mild or moderate: 1 every 12 hours.

c. Mild cognitive impairments (MCI): 1 every 12 hours.
d. Memory disorders associated to aging: 1 every 24 hours.

Example 4

Shilajit's Toxicity in Nerve Cell Culture

The toxicity of the composition's main component was determined, whose toxicity in nerve cells was unknown up to now. This study consisted in the application of concentrations ranging from 10 to 50 mg/mL to a culture of neuroblastoma cells (N-115 cell line) (MTT assay) and subsequent observation of neuronal death through fluorescent microscopy using the calcein-AM method that determines the morphologic integrity. The experiment's results are shown in Table 1.

TABLE 1 viability of neuroblastoma cells in cultures exposed to Shilajit

| Shilajit conc. (μg/ml) | A550* | DE | % neuronal death* |
| --- | --- | --- | --- |
| 0 | 0.315 | 0.025 | 0.0 |
| 10 | 0.320 | 0.020 | 0.0 |
| 50 | 0.340 | 0.015 | 0.0 |
| 100 | 0.295 | 0.030 | 5.5 |
| 250 | 0.300 | 0.020 | 4.7 |
| 500 | 0.310 | 0.030 | 1.4 |
| 10 mM H2O2 (positive control of neuronal death) | 0.050 | 0.010 | 100.0 |

*Average of 5 determinations. From: Results of Cell and Molecular Biology and Neurosciences Laboratory (Dr. R. B. Maccioni).

Results show a very low neuronal death, even at high concentrations of purified shilajit in the culture, which indicates a very low or even null product toxicity.

Example 5

Shilajit's Antioxidant Capacity

Experiments were carried out to determine Shilajit's antioxidant capacity versus known products evaluated through the determination of the absorption capacity of oxygen reactive species (ORAC) using for that fluorescein as a fluorescent probe and employing peroxyl radical as an instrument of evidence. Trolox was used as a comparison standard, a vitamin E analogue in a water-based solution, with which the respective calibration curves were made. The results obtained can be seen in Table 2.

TABLE 2

Absorption capacity of oxygen reactive species (ORAC)

| PRODUCT | Activity (units/g) |
| --- | --- |
| Raisins* | 57.70 |
| Berries* | 20.36 |
| Strawberries* | 15.40 |
| Oranges* | 7.50 |
| Spinach* | 12.60 |
| Brucellas* | 9.80 |
| Shilajit** | 54.71 |
| Shilajitplus** | 144.78 |

Analysis references:
*Ronald Prior, USDA Human Nutrition Research Center on aging at tufts.
**Paolo Strobel, Faculty of Biological Sciences, Catholic University of Chile.

Example 6

Comparative Example between Shilajit and the Invention's Formulation on Neuronal Morphometry For this analysis primary cultures were used of rats' hypocampus cells placed in plate culture and incubated under standard conditions with substrata. The results of the morphometric analysis can be seen in Table 3.

TABLE 3

Morphometric analysis of rats' hypocampus cells, exposed to the invention's formulation.

| | CONTROL | SHILAJIT | INVENTION'S FORMULATION |
| --- | --- | --- | --- |
| Nr. of neuronal cells per field | 367 ± 23 | 345 ± 42 | 396 ± 16 |
| % of cells with neuronal processes | 18 ± 2.1 | 26 ± 3.2 | 43 ± 3.1 |
| Fraction of processes similar to axón | 0.22 | 0, .9 | 0.41 |
| Lengthening processes (mm) | 17.4 ± 7.2 | 26.0 ± 4.5 | 39.6 ± 8.0 |

From: Results of the study on Shilajit and New Nutraceutic Formulation obtained in the Cell and Molecular Biology and Neurosciences Laboratory of the ICC (Dr. R. B. Maccioni).

It can be inferred from the experiment that the invention's formulation shows clear advantages over Shilajit only with respect to control, proving, therefore, a therapeutic efficacy analyzed on the basis of the morphometric characteristics of neuronal cells.

REFERENCE WORKS

R. B. Maccioni & G. Perry (2009) "Current hypotheses and research milestones in Alzheimer's disease". SPRINGER, New York, 296 pp.

R. B. Maccioni, J. Fernandez, L. Rojo and R. Kuljis (2009) "Neuroimmunomodulation in Alzheimer's disease". Ann New York Acad. Sci. 1153: 240-247.

J. Fernandez, L. Rojo, R. O. Kuljis and R. B. Maccioni (2008) "The damage signals hypothesis of Alzheimer's disease pathogenesis". J. Alz. Disease v.14: 329-333.

Dubois B., Feldman H., Jacova C. (2007). Research criteria for the diagnosis of Alzheimer's disease: revising the NINCDS-ADRDA criteria. Lancet Neurol. 6: 734-46.

Green R. C., Cupples L. A., Go R., Benke K. S., Edeki T., Griffith P. A., Williams M., Hipps Y., Graff-Radford N., Bachman D., Farrer L. A. (2002). MIRAGE Study Group. Risk of dementia among white and African American relatives of patients with Alzheimer disease. JAMA. 287 (3): 329-36.

Kurt M. A., Davies D. C., Kidd M. (1997). Paired helical filament morphology varies with intracellular location in Alzheimer's disease brain. Neurosci Lett. 239 (1): 41-4.

Maccioni R. B., Farias G. A., Rojo L. E., Sekler M. A. and Kuljis R. O. (2008a). What have we learned from the tau hypothesis? In: Hypotheses and Research Milestones in Alzheimer's Disease (R. B. Maccioni & G. Perry, Eds.). Springer-Verlag, New York-Heidelberg.

Maccioni R. B., Lavados M., Maccioni C. B. and Mendoza A. (2004). Biological markers of Alzheimer's disease and mild cognitive impairment. Current Alzheimer Research. 1: 307-314.

Maccioni C., Arzola M. E., Mujica L. and Maccioni R. B. (2003). New paradigms in the study of the pathogenesis of Alzheimer's disease. Rev Chil Neuro-Psiquiatr. 41 (2): 33-46.

Maccioni, R. B., Barbeito L., and Munoz J. P. (2001). The molecular bases of Alzheimer's disease and other neurodegenerative disorders. Arch. Medical Research. 32: 367-381.

Mattson M. (2004). Pathways towards and away from Alzheimer disease. Nature. 430 (7000): 631-9. Review.

Rojo L. E., Fernández J. A., Maccioni A. A., Jimenez J. M., Maccioni R. B. (2008). Neuroinflammation: implications for the pathogenesis and molecular diagnosis of Alzheimer's disease. Arch Med Res. 39 (1): 1-16.

Wimp A., Winblad B. (2001). Health economical aspects of Alzheimer disease and its treatment. Psychogeriatrics. 1: 189-93.

Winblad B. (2001). Maintaining functional and behavioral abilities in Alzheimer disease. Alzheimer Dis Assoc Disord. 1: S34-40.

Zambrano C A, Egaña J T, Núñez M T, Maccioni R B, González-Billault C. (2004). Oxidative stress promotes tau dephosphorylation in neuronal cells: the roles of cdk5 and PP1. Free Radic Biol. Med. 36 (11): 1393-402.

The invention claimed is:

1. A method for treating cognitive dysfunction and/or neurodegeneration in a person with senile dementia, Alzheimer's disease, mild cognitive impairment or a memory disorder associated with aging comprising the steps of:
   formulating a composition comprising Andean Shilajit extract in an amount of 250 to 500 milligrams, folic acid in an amount of 200 to 500 micrograms, vitamin B6 in an amount of 20 to 40 milligrams, vitamin B12 in an amount of 4 to 8 micrograms and nutritionally and/or pharmaceutically acceptable excipients; and
   orally administering said composition to said person.

2. The method according to claim 1, wherein said composition is administered to a person with Alzheimer's disease.

3. The method according to claim 1, where said composition is administered to a person with mild or moderate senile dementia.

4. The method according to claim 1, wherein said composition is administered to a person with a mild cognitive disorder.

5. The method according to claim 1, wherein said composition is administered to a person with memory disorders associated with aging.

6. The method of claim 1, wherein said composition is in the form of a food additive or a beverage and is administered to a person with Alzheimer's disease.

7. The method according to claim 1, wherein said composition is in the form of a food additive or a beverage.

8. The method according to claim 7, where said composition is administered to a person with a mild cognitive disorder.

9. The method according to claim 7, wherein said composition is administered to a person with memory disorders associated with aging.

10. The method according to claim 7, wherein said composition is administered to a person with mild or moderate senile dementia.

11. The method of claim 1, wherein the said Andean Shilajit extract is present in an amount of about 250 mg.

12. The method of claim 1, wherein said folic acid is present in an amount of about 200 micrograms.

13. The method of claim 1, wherein said vitamin B12 is present in an amount of about 4 micrograms.

14. The method of claim 1, wherein said vitamin B6 content is present in an amount of about 20 micrograms.

15. The method of claim 1, wherein the composition is in an amount of at least 350 mg by weight.

16. The method of claim 1, wherein said composition is administered in a unit amount every 12 hours to said person with Alzheimer's disease.

17. The method of claim 1, wherein said composition is administered in a unit amount every 24 hours to said person with memory disorders associated with aging.

* * * * *